(12) United States Patent
Levy et al.

(10) Patent No.: US 12,402,905 B2
(45) Date of Patent: Sep. 2, 2025

(54) SERRATED ULTRASONIC CUTTING BLADE WITH VARIED TOOTH PITCH

(71) Applicant: Misonix, LLC, Farmingdale, NY (US)

(72) Inventors: Elad Levy, Amherst, NY (US); Timothy O'Connor, Boca Raton, FL (US); Dan Voic, Cedar Grove, NJ (US)

(73) Assignee: Misonix, LLC, Farmingdale, NY (US)

( * ) Notice: Subject to any disclaimer, the term of this patent is extended or adjusted under 35 U.S.C. 154(b) by 899 days.

(21) Appl. No.: 17/402,295

(22) Filed: Aug. 13, 2021

(65) Prior Publication Data
US 2023/0048993 A1 Feb. 16, 2023

(51) Int. Cl.
*A61B 17/32* (2006.01)

(52) U.S. Cl.
CPC ......... *A61B 17/320068* (2013.01); *A61B 2017/320077* (2017.08)

(58) Field of Classification Search
CPC ......... A61B 2017/32006; A61B 17/14; A61B 17/142; A61B 17/144; A61B 17/149; A61B 17/01; B27B 19/008; B27B 19/006
See application file for complete search history.

(56) References Cited

U.S. PATENT DOCUMENTS

| | | |
|---|---|---|
| 2,349,959 A | 5/1944 | Edward |
| 2,753,666 A | 7/1956 | Sasse |
| 3,368,280 A | 2/1968 | Friedman et al. |
| 3,680,610 A * | 8/1972 | Lindgren ............ B23D 1/126 30/502 |
| 3,805,787 A | 4/1974 | Banko |
| 4,188,952 A | 2/1980 | Loschilov et al. |
| 4,425,115 A | 1/1984 | Wuchinich |
| 4,804,364 A | 2/1989 | Dieras et al. |
| 4,988,334 A | 1/1991 | Hornlein et al. |
| 5,163,433 A | 11/1992 | Kagawa et al. |
| 5,176,677 A | 1/1993 | Wuchinich |
| 5,180,363 A | 1/1993 | Idemoto et al. |
| 5,222,937 A | 6/1993 | Kagawa |
| 5,261,922 A | 11/1993 | Hood |
| 5,312,329 A | 5/1994 | Beaty et al. |
| 5,342,380 A | 8/1994 | Hood |

(Continued)

FOREIGN PATENT DOCUMENTS

| | | | |
|---|---|---|---|
| CN | 210249992 U | 4/2020 | |
| CN | 109152577 B * | 1/2022 | ......... A61B 17/1644 |

(Continued)

OTHER PUBLICATIONS

Extended European Search Report for EP Application No. 22856601.4, dated Apr. 16, 2025, 5 pages.

(Continued)

*Primary Examiner* — Ashley L Fishback
(74) *Attorney, Agent, or Firm* — COOLEY LLP

(57) ABSTRACT

An ultrasonic blade is provided along a convexly arcuate distal edge and at least one longitudinal edge with a continuous array of teeth including a first subset of teeth along the convexly arcuate distal edge and a second subset of teeth along the at least one straight longitudinal edge. The teeth along the convexly arcuate distal edge differ in tooth length and optionally in inter-tooth separation or pitch from the teeth along one or both of the longitudinal edges.

20 Claims, 2 Drawing Sheets

(56) References Cited

U.S. PATENT DOCUMENTS

| | | |
|---|---|---|
| 5,465,468 A | 11/1995 | Manna |
| 5,484,398 A | 1/1996 | Stoddard |
| 5,517,889 A | 5/1996 | Logan |
| 5,527,273 A | 6/1996 | Manna et al. |
| 5,531,597 A | 7/1996 | Foulkes et al. |
| 5,769,211 A | 6/1998 | Manna et al. |
| 5,906,595 A | 5/1999 | Powell et al. |
| 5,935,142 A | 8/1999 | Hood |
| 5,935,143 A | 8/1999 | Hood |
| 5,976,105 A | 11/1999 | Marcove et al. |
| 6,036,667 A | 3/2000 | Manna et al. |
| 6,256,859 B1 | 7/2001 | Stoddard et al. |
| 6,270,471 B1 | 8/2001 | Hechel et al. |
| 6,352,532 B1 | 3/2002 | Kramer et al. |
| 6,375,648 B1 | 4/2002 | Edelman et al. |
| 6,379,371 B1 | 4/2002 | Novak et al. |
| 6,436,114 B1 | 8/2002 | Novak et al. |
| 6,454,730 B1 | 9/2002 | Hechel et al. |
| 6,461,314 B1 | 10/2002 | Pant et al. |
| 6,492,762 B1 | 12/2002 | Pant et al. |
| 6,494,714 B1 | 12/2002 | Copeland |
| 6,582,440 B1 | 6/2003 | Brumbach |
| 6,602,248 B1 | 8/2003 | Sharps et al. |
| 6,613,056 B1 | 9/2003 | Brumbach et al. |
| 6,736,814 B2 | 5/2004 | Manna et al. |
| 6,799,729 B1 | 10/2004 | Voic |
| 6,869,439 B2 | 3/2005 | White et al. |
| 7,025,735 B2 | 4/2006 | Soring et al. |
| 7,223,267 B2 | 5/2007 | Isola et al. |
| 7,431,704 B2 | 10/2008 | Babaev |
| 7,442,168 B2 | 10/2008 | Novak et al. |
| 7,494,488 B2 | 2/2009 | Weber |
| 7,522,955 B2 | 4/2009 | Rontal |
| 7,608,054 B2 | 10/2009 | Söring et al. |
| 7,717,913 B2 | 5/2010 | Novak et al. |
| 7,776,027 B2 | 8/2010 | Manna et al. |
| 7,785,278 B2 | 8/2010 | Babaev |
| D627,463 S | 11/2010 | Voic et al. |
| 7,905,854 B2 | 3/2011 | Hazut et al. |
| 7,931,611 B2 | 4/2011 | Novak et al. |
| D644,326 S | 8/2011 | Voic et al. |
| 8,025,672 B2 | 9/2011 | Novak et al. |
| 8,109,925 B2 | 2/2012 | Voic et al. |
| 8,221,424 B2 | 7/2012 | Cha |
| D667,117 S | 9/2012 | Darian et al. |
| 8,343,178 B2 | 1/2013 | Novak et al. |
| 8,348,880 B2 | 1/2013 | Messerly et al. |
| 8,353,912 B2 | 1/2013 | Darian et al. |
| 8,430,897 B2 | 4/2013 | Novak et al. |
| 8,562,547 B2 | 10/2013 | Babaev |
| 8,659,208 B1 | 2/2014 | Rose et al. |
| 8,690,783 B2 | 4/2014 | Sinelnikov |
| 8,698,377 B2 | 4/2014 | Sinelnikov |
| 8,814,870 B2 | 8/2014 | Paraschiv et al. |
| 8,888,783 B2 | 11/2014 | Young |
| 8,894,673 B2 | 11/2014 | Darian |
| 8,961,547 B2 | 2/2015 | Dietz et al. |
| 9,211,137 B2 | 12/2015 | Voic |
| 9,226,767 B2 | 1/2016 | Stulen et al. |
| 9,320,528 B2 | 4/2016 | Voic et al. |
| 9,387,005 B2 | 7/2016 | Voic |
| 9,603,656 B1 | 3/2017 | Germain et al. |
| 9,622,766 B2 | 4/2017 | Voic |
| 9,636,187 B2 | 5/2017 | Voic |
| 9,693,792 B2 | 7/2017 | Novak et al. |
| 9,763,673 B2 | 9/2017 | Young |
| 9,861,446 B2 | 1/2018 | Lang |
| 9,872,697 B2 | 1/2018 | Voic |
| 9,949,751 B2 | 4/2018 | Voic |
| 9,962,182 B2 | 5/2018 | Dietz et al. |
| 10,016,208 B2 | 7/2018 | Gouery et al. |
| 10,076,349 B2 | 9/2018 | Voic |
| 10,092,741 B2 | 10/2018 | Darian |
| 10,117,666 B2 | 11/2018 | Voic |
| 10,182,837 B2 | 1/2019 | Isola et al. |
| 10,206,704 B2 | 2/2019 | Voic et al. |
| 10,299,809 B2 | 5/2019 | Mikus et al. |
| 10,398,463 B2 | 9/2019 | Darian et al. |
| 10,398,465 B2 | 9/2019 | Darian |
| 10,405,875 B2 | 9/2019 | Voic et al. |
| 10,463,381 B2 | 11/2019 | Voic et al. |
| 10,470,788 B2 | 11/2019 | Sinelnikov |
| 10,470,789 B2 | 11/2019 | Mikus et al. |
| 10,471,281 B2 | 11/2019 | Mikus |
| 10,543,012 B2 | 1/2020 | Pantano |
| 10,588,691 B2 | 3/2020 | Pellegrino et al. |
| 10,639,733 B2 * | 5/2020 | Campbell ............ B23D 61/126 |
| 10,687,824 B2 | 6/2020 | Shiels et al. |
| 10,835,276 B2 | 11/2020 | Voic et al. |
| 10,842,587 B2 | 11/2020 | Mikus et al. |
| 11,007,308 B2 | 5/2021 | Payne et al. |
| 11,298,434 B2 | 4/2022 | Isola et al. |
| 11,324,531 B2 | 5/2022 | Voic et al. |
| 11,672,558 B2 | 6/2023 | Voic |
| 11,950,790 B2 | 4/2024 | Voic |
| 12,011,190 B2 | 6/2024 | Theodore et al. |
| 2001/0029370 A1 | 10/2001 | Hodva et al. |
| 2003/0212395 A1 | 11/2003 | Woloszko et al. |
| 2004/0265776 A1 | 12/2004 | Tipton et al. |
| 2005/0033292 A1 | 2/2005 | Teitelbaum et al. |
| 2006/0030797 A1 | 2/2006 | Zhou et al. |
| 2006/0235305 A1 | 10/2006 | Cotter et al. |
| 2006/0241533 A1 | 10/2006 | Geller |
| 2007/0060926 A1 | 3/2007 | Escaf |
| 2007/0213734 A1 | 9/2007 | Bleich et al. |
| 2008/0015551 A1 | 1/2008 | Feine |
| 2008/0057470 A1 | 3/2008 | Levy et al. |
| 2008/0058775 A1 | 3/2008 | Darian et al. |
| 2008/0108985 A1 | 5/2008 | Konesky |
| 2008/0183173 A1 | 7/2008 | Jozat |
| 2008/0234709 A1 | 9/2008 | Houser |
| 2008/0234710 A1 | 9/2008 | Neurohr et al. |
| 2009/0143678 A1 | 6/2009 | Keast et al. |
| 2010/0022944 A1 | 1/2010 | Wilcox |
| 2010/0049188 A1 | 2/2010 | Nelson et al. |
| 2010/0076349 A1 | 3/2010 | Babaev |
| 2011/0092880 A1 | 4/2011 | Gertner |
| 2011/0105958 A1 | 5/2011 | Babaev |
| 2011/0160624 A1 | 6/2011 | Babaev |
| 2011/0264090 A1 | 10/2011 | Shadduck et al. |
| 2012/0014868 A1 | 1/2012 | Roy |
| 2012/0053492 A1 | 3/2012 | Chang et al. |
| 2013/0103021 A1 | 4/2013 | Germain et al. |
| 2013/0123774 A1 | 5/2013 | Zadeh |
| 2013/0231528 A1 | 9/2013 | Voic |
| 2013/0245638 A1 | 9/2013 | Horton et al. |
| 2014/0107537 A1 | 4/2014 | Beaupre |
| 2014/0277030 A1 | 9/2014 | Lauchner |
| 2014/0277034 A1 | 9/2014 | Darian |
| 2014/0350567 A1 | 11/2014 | Schmitz et al. |
| 2014/0358043 A1 | 12/2014 | Akagane |
| 2015/0066032 A1 | 3/2015 | Young |
| 2015/0088137 A1 | 3/2015 | Manna |
| 2015/0094723 A1 | 4/2015 | Darian |
| 2015/0157387 A1 | 6/2015 | OuYang et al. |
| 2015/0164534 A1 | 6/2015 | Felder et al. |
| 2015/0297246 A1 | 10/2015 | Patel et al. |
| 2016/0022283 A1 | 1/2016 | Wallace et al. |
| 2016/0135835 A1 | 5/2016 | Onuma |
| 2016/0166276 A1 | 6/2016 | Huang et al. |
| 2016/0175150 A1 | 6/2016 | Banko |
| 2016/0206302 A1 | 7/2016 | Eckermann |
| 2016/0222526 A1 | 8/2016 | Rubinsky et al. |
| 2016/0331439 A1 | 11/2016 | Winkelman et al. |
| 2016/0354559 A1 | 12/2016 | Gavini et al. |
| 2017/0340339 A1 | 11/2017 | Madan et al. |
| 2018/0008138 A1 | 1/2018 | Thommen et al. |
| 2019/0000553 A1 | 1/2019 | Lightcap et al. |
| 2019/0307529 A1 | 10/2019 | Jacoby |
| 2020/0121374 A1 | 4/2020 | McGahan et al. |
| 2020/0178999 A1 | 6/2020 | Stabilini et al. |
| 2020/0205850 A1 | 7/2020 | Cao et al. |
| 2020/0246056 A1 | 8/2020 | Bonn |
| 2020/0405501 A1 | 12/2020 | Orozco Castillo |

(56) References Cited

U.S. PATENT DOCUMENTS

| | | |
|---|---|---|
| 2021/0145531 A1 | 5/2021 | Gee et al. |
| 2021/0267622 A1 | 9/2021 | Ellegala |
| 2023/0210549 A1 | 7/2023 | Voic et al. |

FOREIGN PATENT DOCUMENTS

| | | | |
|---|---|---|---|
| EP | 2745797 A1 | 6/2014 | |
| EP | 2635192 B1 | 3/2019 | |
| JP | H0614934 A | 1/1994 | |
| JP | H10127682 A | 5/1998 | |
| KR | 20120093654 A | 8/2012 | |
| WO | WO-2004060141 A2 | 7/2004 | |
| WO | WO-2007049718 A1 | 5/2007 | |
| WO | WO-2008014258 A2 * | 1/2008 | ........... A61B 17/144 |
| WO | WO-2008017909 A1 | 2/2008 | |
| WO | WO-2008118708 A2 | 10/2008 | |
| WO | WO-2008118709 A1 | 10/2008 | |
| WO | WO-2009035508 A1 | 3/2009 | |
| WO | WO-2009098664 A2 | 8/2009 | |
| WO | WO-2009105628 A2 | 8/2009 | |
| WO | WO-2010109447 A1 | 9/2010 | |
| WO | WO-2013062118 A1 | 5/2013 | |
| WO | WO-2014024550 A1 | 2/2014 | |
| WO | WO-2015045198 A1 | 4/2015 | |
| WO | WO-2015046349 A1 | 4/2015 | |
| WO | WO-2015145444 A2 | 10/2015 | |
| WO | WO-2015188735 A1 | 12/2015 | |
| WO | WO-2017180493 A1 | 10/2017 | |
| WO | WO-2019095831 A1 | 5/2019 | |
| WO | WO-2023018863 A1 | 2/2023 | |

OTHER PUBLICATIONS

International Preliminary Report on Patentability for Application No. PCT/US2022/040047, dated Feb. 22, 2024, 6 pages.

International Search Report and Written Opinion for Application No. PCT/US2022/040047, dated Nov. 30, 2022, 7 pages.

SonicOne O.R., Ultrasonic Surgical Debridement. Brochure [online]. Misonix Ultrasonic Surgical Devices, 2012. Retrieved from the Internet: <URL: https://web.archive.org/web/20150218182717/http://www.misonix.com:80/wp-content/uploads/2013/11/SO-OR_2003-12_REV_A_SonicOne_OR_Brochure.pdf>, 6 Pages.

SonicOne Plus, Ultrasonic Debridement System. Brochure [online]. Misonix Ultrasonic Surgical Devices, 2013. Retrieved from the Internet: <URL: https://pdf.medicalexpo.com/pdf/misonix/sonicone-plus/79244-106567.html>, 4 pages.

* cited by examiner

SERRATED ULTRASONIC CUTTING BLADE WITH VARIED TOOTH PITCH

FIELD OF THE INVENTION

This invention relates to an ultrasonic tool. More particularly, this invention relates to an ultrasonic cutting blade. The blade is particularly useful in a surgical application to cut tissue such as cartilage and bone.

BACKGROUND OF THE INVENTION

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line. Over several centuries, these tasks were performed through the utilization of devices called bone saws.

Traditional bone saws are categorized into several basic categories. Hand powered saws or drills are just that, hand held devices which require the operator to move the device in a fashion similar to that used for carpentry tools. Powered devices, whether electric or pneumatic, are of either the reciprocating or rotary type. The reciprocating devices use a flat, sword like blade where the back and forth motion is provided by a motor instead of the hand. The rotary devices use a rotating motor to spin a drill bit or a blade that has teeth arranged around its circumference similar to a table saw blade. All of these traditional bone saws are used today in medical procedures around the world.

While traditional saws are functional, they have many disadvantages. With either the band or reciprocating saws, for instance, it is not easy to initiate and direct a cut. A cut must start from an edge or, alternatively, a starting hole must be used. To create a starting hole, a drill or similar instrument is operated to bore into the bone. Subsequently, a cutting blade is inserted into the bored hole. The user can then proceed to cut. Alternatively, a rotary type blade may be used. However, when a rotary blade is used, the cut must follow a relatively straight path to prevent the blade from binding in the cut. With all blades the ability to create a curved or compound angle cut is extremely limited by the blade chosen. The relatively thick blades have a wide kerf, so that a significant thickness of the viable bone is lost in the cutting procedure. Physicians would like this width to be as thin as possible in most procedures where reconstruction is necessary.

Ultrasonic bone cutting blades as disclosed, for example, in U.S. Pat. Nos. 5,261,922; 6,379,371; 6,443,969; 6,763,673; 8,888,783; 9,387,005; 9,320,528; D680,218; and D667,117 overcome many of the disadvantages and problems discussed above. However room for improvement remains. One problem is that surgeons sometimes have difficulty in penetrating into particularly large and strong bone structures, including spinal vertebrae and spinal lamina and processes.

OBJECTS OF THE INVENTION

It is an object of the present invention to provide an improved ultrasonic surgical tool or probe for ablating or dissecting osseous tissue and cartilage.

Another object of the present invention is to provide such an ultrasonic surgical tool or probe that more readily facilitates bone cutting procedures, particularly, but not exclusively, spinal bone cutting procedures.

Yet another object of the present invention is to provide such an ultrasonic surgical tool or probe that is less likely to cut non-osseous tissue than bone.

Yet another object of the present invention is to provide a surgical disc space preparation procedure that may be used to access spinal discs in surgical procedures.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

An ultrasonic surgical tool in accordance with the present invention comprises a substantially planar blade body having a pair of opposed lateral surfaces, a pair of straight longitudinal edges, and a convexly arcuate distal edge contiguous with the straight longitudinal edges. A shank is integral on a distal side with the blade body and provided at a proximal side with a connector for operatively linking the blade to a source of ultrasonic mechanical vibrations. The blade body is provided along the convexly arcuate distal edge and at least one of the straight longitudinal edges with a continuous array of teeth including a first subset of teeth along the convexly arcuate distal edge and a second subset of teeth along the at least one straight longitudinal edge. The first subset of teeth exhibits a first tooth length and a first inter-tooth gap depth, while the second subset of teeth has a second tooth length and a second inter-tooth gap depth. The first tooth length differs from the second tooth length, and the first inter-tooth gap depth differs from the second inter-tooth gap depth.

Another feature of an ultrasonic surgical tool in accordance with the present invention is that the first tooth length and the first inter-tooth gap depth are each uniform among the first subset of teeth, while the second tooth length and the second inter-tooth gap depth are each uniform among the second subset of teeth.

Pursuant to another feature of the present invention, the first tooth length and the first inter-tooth gap depth are smaller than the second tooth length and the second inter-tooth gap depth, respectively. Specifically, the first tooth length is between about 0.60 and about 0.85 times the second tooth length, and the first inter-tooth gap depth is between about 0.60 and about 0.85 times the second inter-tooth gap depth. Preferably, the first tooth length is about 0.80 times the second tooth length, and the first inter-tooth gap depth is about 0.80 times the second inter-tooth gap depth.

As indicated above, the first tooth length and the first inter-tooth gap depth may be uniform among the first subset of teeth, while the second tooth length and the second inter-tooth gap depth are uniform among the second subset of teeth. However, this is not invariably the case. For instance, the first tooth length and the first inter-tooth gap depth may vary from a minimum at an extreme distal tip of the arcuate distal edge and increase gradually on each side towards the respective longitudinal edge of the blade.

In a preferred embodiment of the invention, the teeth of the continuous array of teeth are all isometrically triangular and bear a common angle between opposing edges. In that event, where the characteristic tooth length of the first subset of teeth is smaller than the characteristic tooth length of the first subset of teeth, the pitch of the teeth of the first subset, along the distal edge of the blade, is necessarily smaller than the pitch of the teeth of the second subset, along one or two longitudinal edges of the blade.

Pursuant to this preferred embodiment, an ultrasonic surgical tool in accordance with the present invention comprises a substantially planar blade body having a pair of opposed lateral surfaces, a pair of straight longitudinal edges and a convexly arcuate distal edge contiguous with the straight longitudinal edges, with a shank integral on a distal side with the blade body being provided at a proximal side with a connector for operatively linking the blade to a source of ultrasonic mechanical vibrations. The blade body is provided along the convexly arcuate distal edge and at least one of the straight longitudinal edges with a continuous array of teeth including a first subset of teeth along the convexly arcuate distal edge and a second subset of teeth along the at least one of the straight longitudinal edges. The first subset of teeth exhibit a first inter-tooth separation or pitch and the second subset of teeth has a second inter-tooth separation, wherein the first inter-tooth separation or pitch differs from the second inter-tooth separation or pitch.

In accordance with a further feature of the present invention, the first inter-tooth separation or pitch is uniform among the first subset of teeth, and the second inter-tooth separation or pitch is uniform among the second subset of teeth.

Pursuant to a more specific feature of the present invention, the first inter-tooth separation or pitch is smaller than the second inter-tooth separation or pitch. The teeth of the continuous array of teeth are preferably all isometrically triangular and may bear a common angle between opposing edges.

Preferably, the first inter-tooth separation or pitch is between about 0.60 and about 0.85 times the second inter-tooth separation or pitch.

An ultrasonic tool in accordance with the present invention facilitates the performance of spinal surgeries, particularly by reducing the likelihood of damage to non-target soft tissue. It is believed that the smaller tooth length along the distal tip of the blade is less aggressive than longer tooth lengths against tissue not intended for removal, such as soft tissue of the spine.

While a uniform tooth sharpness (per the angle between relatively inclined tooth edges) is preferred, largely for manufacturing reasons, it is contemplated that the tooth angle may be reduced along the longitudinal edges to reduce the pitch and thereby increase the fineness of cutting and produce a smoother kerf.

DETAILED DESCRIPTION

Figure 1:
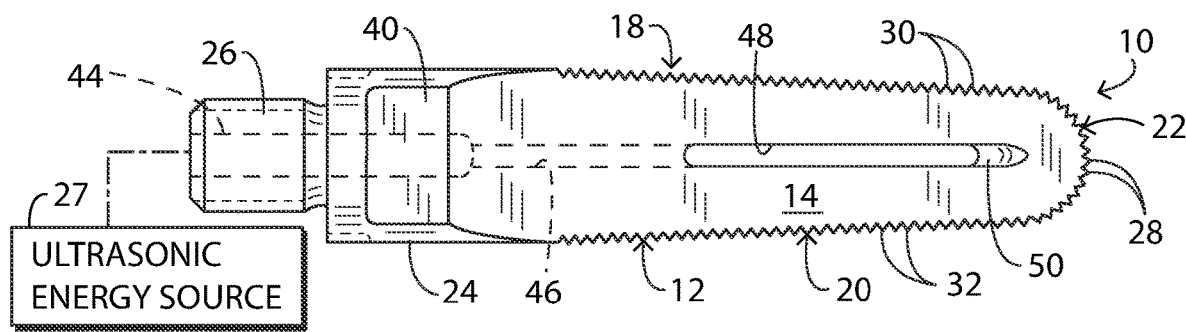
FIG. 1 is a top plan view of an ultrasonic surgical tool or probe, particularly an ultrasonic surgical blade, in accordance with the present invention, a bottom plan view being identical to the top plan view.
Figure 2:
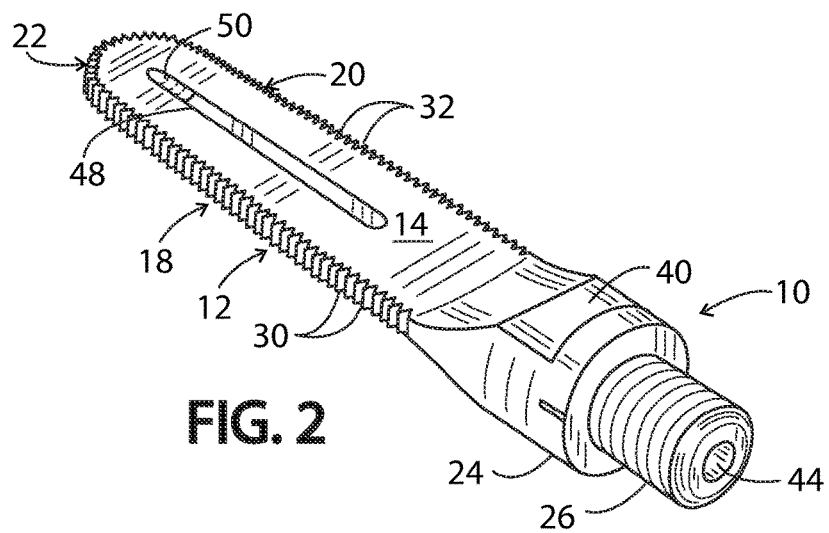
FIG. 2 is a rear, left side and top perspective view of the ultrasonic surgical tool or probe of FIG. 1.
Figure 3:
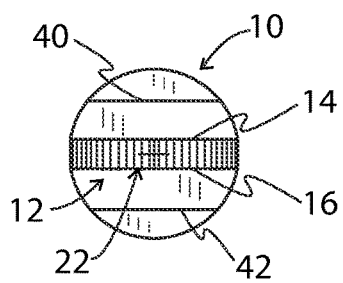
FIG. 3 is a front elevational view of the ultrasonic surgical tool or probe of FIGS. 1 and 2.
Figure 4:
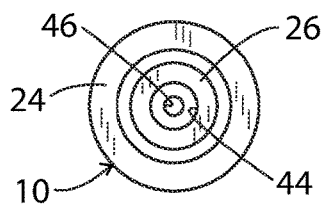
FIG. 4 is a rear elevational view of the ultrasonic surgical tool or probe of FIGS. 1-3.
Figure 5:
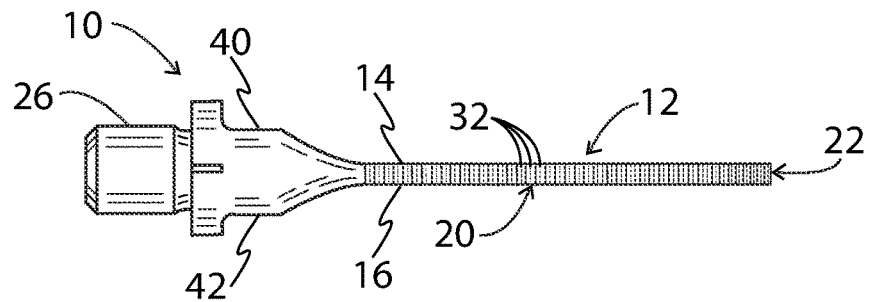
FIG. 5 is a right side elevational view of the ultrasonic surgical tool or probe of FIGS. 1-4, a left side elevation view being identical thereto.
Figure 6:
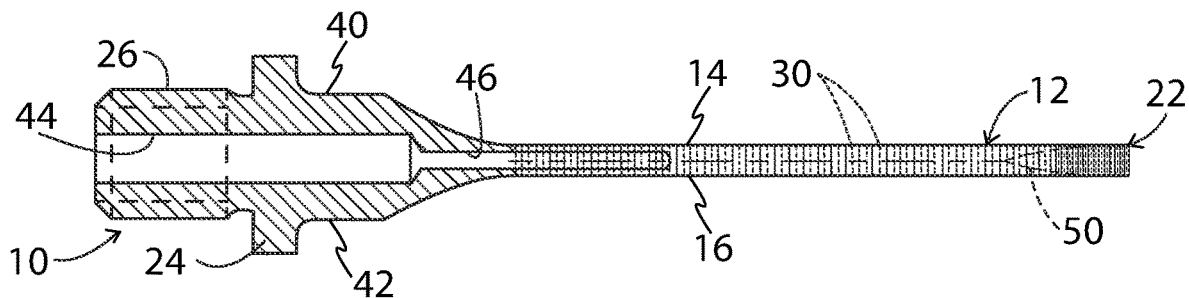
FIG. 6 is longitudinal axial cross-sectional view of the ultrasonic surgical tool or probe of FIGS. 1-5.

As depicted in the drawings, an ultrasonic surgical tool or probe 10 includes a substantially planar blade body 12 having a pair of parallel opposed lateral surfaces or major faces 14 and 16, a pair of straight substantially longitudinal edges 18 and 20, and a convexly arcuate distal edge 22 contiguous and continuous with the straight longitudinal edges. Longitudinal edges 18 and 20 converge slightly towards one another at the distal end of blade body 12; longitudinal edges 18 and 20 are oriented at an angle of several degrees of arc relative to one another.

A transversely enlarged proximal portion or shank 24 is integral on a distal side with blade body 12 and provided on a proximal side with an externally threaded connector 26 for operatively coupling the blade body ("blade") 12 to a source 27 of ultrasonic mechanical vibratory energy, particularly to a stack of piezoelectric crystal elements (not shown) and a waveform generator (not shown) that applies an ultrasonic-frequency voltage across the piezo-stack. Shank 24 is formed with a pair of opposed flats 40, 42 engageable by a wrench (not illustrated) for screwing the tool or probe 10 to an ultrasonic handpiece and particularly the piezoelectric crystal stack therein.

Shank 24 and blade body 12 are formed with co-linear channels, bores or lumens 44 and 46 of different diameters that communicate with one another and at a distal end with a through slot 48 extending longitudinally and axially along a portion of blade body 12. Liquid coolant, typically aqueous, is conveyed through channels 44 and 46 to slot 48 for maintaining the temperature of blade 12 and or adjacent biological tissue within a biologically safe range.

Blade body 12 is provided along convexly arcuate distal edge 22 and at least one but preferably both longitudinal edges 18 and 20 with a continuous array of teeth including a first subset of teeth 28 along convexly arcuate distal edge 22 and a second subset of teeth 30, 32 along longitudinal edges 18 and 20. Teeth 28 exhibit a first tooth length TL1 and an associated first inter-tooth gap depth (not designated) typically equal to one another, while teeth 30 and 32 have a second tooth length TL2 and a second inter-tooth gap depth (not designated) generally equal thereto. Tooth length TL1 differs from the tooth length TL2, and concomitantly the first inter-tooth gap depth differs from the second inter-tooth gap depth. A conically tapered surface 50 at a distal end of through slot 48 serves to distribute coolant to arcuate edge 22 along the length thereof.

Preferably, but not necessarily, tooth length TL1 and the associated inter-tooth gap depth are each uniform among teeth 28, while tooth length TL2 and the associated inter-tooth gap depth are each uniform among at least teeth 30 or 32. However, the lengths of teeth 28 and the associated first inter-tooth gap depth may vary from a minimum at an extreme distal tip of arcuate distal edge 22 and increase gradually on each side towards the respective longitudinal edge 30, 32 of blade body 12. Or one might provide teeth 30 and teeth 32 with different common tooth lengths TL2 and inter-tooth gap depths, where an application targets a region of different bone structures or densities.

Preferably, tooth length TL1 and the inter-tooth gap depth of teeth 28 are respectively smaller than tooth length TL2 and the inter-tooth gap depth of teeth 30, 32. Specifically, tooth length TL1 lies between approximately 0.60 and approximately 0.85 times tooth length TL2, the associated inter-tooth gap depths exhibiting the same proportionality. Preferably, tooth length TL1 is about 0.80 times tooth length TL2, for instance, where tooth length TL1 is 0.0016 inch while tooth length TL2 is 0.0020 inch. Concomitantly, the inter-tooth gap depth of teeth 28 is 0.80 times the second inter-tooth gap depth of teeth 30 and/or 32.

Teeth 28, 30, 32 are preferably all isometrically triangular and bear a common angle a1, a2 between opposing edges. This geometric congruence simplifies manufacture. However, angles a1 and a2 may differ from one another. For instance, angle a1 may be larger than angle a2. Where the tooth length TL2 is unchanged, the reduction in the angle a2 and the consequent increase in sharpness of teeth 30, 32 correlates to a reduction in a pitch TP2 thereof. Such a reduction in pitch may be implemented to increase the fineness of cutting action of edges 30, 32.

Thus, an ultrasonic surgical tool in accordance with the present invention comprises planar blade body 12 with opposed lateral surfaces 14 and 16, straight longitudinal edges 18 and 20 and convexly arcuate distal edge 22 contiguous with edges 18 and 20, with shank 24 integral on a distal side with blade body 12 and provided with connector 26 for operatively linking blade 12 to vibration source 27. As described above, blade body 12 is provided along convexly arcuate distal edge 22 and at least one of longitudinal edges 18, 20 with a continuous array of teeth including teeth 28 along distal edge 22 and teeth 30, 32 along longitudinal edges 30, 32. Teeth 28 exhibit a first inter-tooth separation or pitch TP1 and teeth 30 and/or 32 has a second inter-tooth separation or pitch TP2 which may be different from inter-tooth separation or pitch TP1.

In a preferred embodiment, inter-tooth separation or pitch TP1 is uniform among teeth 28, while inter-tooth separation or pitch TP2 is uniform among teeth 30 and/or 32. Inter-tooth separation or pitch TP1 is smaller than inter-tooth separation or pitch TP2, where the teeth of the continuous array of teeth are all isometrically triangular and bear a common angle between opposing edges (a1=a2, exemplarily 60°). Alternatively, one might vary the manufacture, particularly the size of angles a1 and a2, so that pitches TP1 and TP2 are the same.

Ultrasonic tool or probe 10 enables a finer control of ablation in spinal surgery by reducing the action of the probe on tissues distal of blade body 12. The shorter tooth length TL1 renders arcuate edge 22 less aggressive, reducing the distal cutting action in relative to the rapidity of ultrasonic cutting along longitudinal edges 18 and 20.

Figure 7:
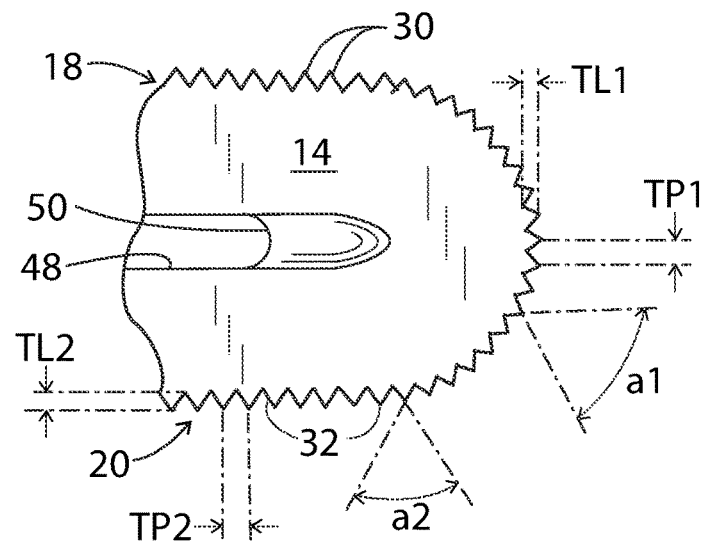
FIG. 7 is partial top or bottom plan view thereof, on an enlarged scale, showing detail VI in FIG. 1.

Although the invention has been described in terms of particular embodiments and applications, one of ordinary skill in the art, in light of this teaching, can generate additional embodiments and modifications without departing from the spirit of or exceeding the scope of the claimed invention. For instance, the pitch and the tooth length (or depth or height) may gradually vary from characteristic values along edges 30 and 32 to different characteristic values along leading or distal edge 22. Alternatively, as indicated schematically in FIG. 7, the change may occur in a single step at a first given point between edges 18 and 22 and at another demarcated point between edges 20 and 22. Accordingly, it is to be understood that the drawings and descriptions herein are proffered by way of example to facilitate comprehension of the invention and should not be construed to limit the scope thereof.

What is claimed is:

1. An ultrasonic surgical tool, comprising:
a substantially planar blade body having a pair of opposed lateral surfaces, a pair of straight longitudinal edges and a convexly arcuate distal edge contiguous with said straight longitudinal edges; and
a shank integral on a distal side with said blade body and provided at a proximal side with a connector for operatively linking the blade to a source of ultrasonic mechanical vibrations,
said substantially planar blade body defining a through slot that extends longitudinally and axially along a portion of the substantially planar blade body, the through slot being configured to deliver a fluid to an area adjacent to the substantially planar blade body,
said substantially planar blade body including an array of teeth disposed along said convexly arcuate distal edge and at least one straight longitudinal edge of said pair of straight longitudinal edges, the array of teeth including a first subset of teeth disposed along said convexly arcuate distal edge and a second subset of teeth disposed along said at least one straight longitudinal edge of said pair of straight longitudinal edges.

2. The ultrasonic surgical tool defined in claim 1, wherein said first tooth length and said first inter-tooth gap depth are each uniform among said first subset of teeth, and said second tooth length and said second inter-tooth gap depth being each uniform among said second subset of teeth.

3. The ultrasonic surgical tool defined in claim 2, wherein said first tooth length and said first inter-tooth gap depth are smaller than said second tooth length and said second inter-tooth gap depth, respectively.

4. The ultrasonic surgical tool defined in claim 3, wherein said first tooth length is between about 0.60 and about 0.85 times said second tooth length, said first inter-tooth gap depth being between about 0.60 and about 0.85 times said second inter-tooth gap depth.

5. The ultrasonic surgical tool defined in claim 4, wherein said first tooth length is about 0.80 times said second tooth length, said first inter-tooth gap depth being about 0.80 times said second inter-tooth gap depth.

6. The ultrasonic surgical tool defined in claim 3, wherein each tooth of said array of teeth includes isometric opposing edges that form a common angle therebetween, each tooth of said first subset of teeth having a first pitch and each tooth of said second subset of teeth having a second pitch, said first pitch being smaller than said second pitch.

7. The ultrasonic surgical tool defined in claim 1, wherein said first tooth length and said first inter-tooth gap depth are smaller than said second tooth length and said second inter-tooth gap depth, respectively.

8. The ultrasonic surgical tool defined in claim 7, wherein said first tooth length is between about 0.60 and about 0.85 times said second tooth length, said first inter-tooth gap depth being between about 0.60 and about 0.85 times said second inter-tooth gap depth.

9. The ultrasonic surgical tool defined in claim 8, wherein said first tooth length is about 0.80 times said second tooth length, said first inter-tooth gap depth being about 0.80 times said second inter-tooth gap depth.

10. The ultrasonic surgical tool defined in claim 7, wherein each tooth of said array of teeth includes isometric opposing edges that form a common angle therebetween, each tooth of said first subset of teeth having a first pitch and each tooth of said second subset of teeth having a second pitch, said first pitch being smaller than said second pitch.

11. The ultrasonic surgical tool defined in claim 1, wherein each tooth of said array of teeth includes isometric opposing edges that form a common angle therebetween, each tooth of said first subset of teeth having a first pitch and each tooth of said second subset of teeth having a second pitch different from said first pitch.

12. The ultrasonic surgical tool defined in claim 1, wherein said first subset of teeth having a first tooth length and a first inter-tooth gap depth, said second subset of teeth having a second tooth length and a second inter-tooth gap depth, said first tooth length being different from said second tooth length, said first inter-tooth gap depth being different from said second inter-tooth gap depth.

13. An ultrasonic surgical tool, comprising:
a substantially planar blade body having a pair of opposed lateral surfaces, a pair of straight longitudinal edges and a convexly arcuate distal edge contiguous with said straight longitudinal edges; and
a shank integral on a distal side with said blade body and provided at a proximal side with a connector for operatively linking the blade to a source of ultrasonic mechanical vibrations,
said substantially planar blade body defining a through slot that extends longitudinally and axially along a portion of the substantially planar blade body, the through slot being configured to deliver a fluid to an area adjacent to the substantially planar blade body,
said substantially planar blade body including an array of teeth disposed along said convexly arcuate distal edge and at least one straight longitudinal edge of said pair of straight longitudinal edges, the array of teeth including a first subset of teeth disposed along said convexly arcuate distal edge and a second subset of teeth disposed along at least one straight longitudinal edge of said pair of straight longitudinal edges,
said first subset of teeth exhibiting a first inter-tooth separation or pitch and said second subset of teeth having a second inter-tooth separation, said first inter-tooth separation or pitch being different from said second inter-tooth separation or pitch.

14. The ultrasonic surgical tool defined in claim 13, wherein said first inter-tooth separation or pitch is uniform among said first subset of teeth, and said second inter-tooth separation or pitch is uniform among said second subset of teeth.

15. The ultrasonic surgical tool defined in claim 14, wherein said first inter-tooth separation or pitch is smaller than said second inter-tooth separation or pitch.

16. The ultrasonic surgical tool defined in claim 15, wherein each tooth of said array of teeth includes isometric opposing edges that form a common angle therebetween.

17. The ultrasonic surgical tool defined in claim 14, wherein said first inter-tooth separation or pitch is between 0.60 and 0.85 times said second inter-tooth separation or pitch.

18. The ultrasonic surgical tool defined in claim 13, wherein said first inter-tooth separation or pitch is smaller than said second inter-tooth separation or pitch.

19. The ultrasonic surgical tool defined in claim 18, wherein said first inter-tooth separation or pitch is between 0.60 and 0.85 times said second inter-tooth separation or pitch.

20. The ultrasonic surgical tool defined in claim 13, wherein each tooth of said array of teeth includes isometric opposing edges that form a common angle therebetween.

* * * * *